United States Patent [19]

Tahara et al.

[11] Patent Number: 4,578,397
[45] Date of Patent: Mar. 25, 1986

[54] INDENO(1,2-B)PYRROLE DERIVATIVES

[75] Inventors: Tetsuya Tahara, Nakatsu; Masafumi Arita, Tokyo, both of Japan

[73] Assignee: Yoshitomi Pharmaceutical Industries, Ltd., Osaka, Japan

[21] Appl. No.: 609,355

[22] PCT Filed: Aug. 30, 1983

[86] PCT No.: PCT/JP83/00287
§ 371 Date: May 7, 1984
§ 102(e) Date: May 7, 1984

[87] PCT Pub. No.: WO84/00962
PCT Pub. Date: Mar. 15, 1984

[30] Foreign Application Priority Data

Sep. 8, 1982 [JP] Japan .................. 57-156997

[51] Int. Cl.⁴ .................. A61K 31/40; C07D 209/70
[52] U.S. Cl. .................. 514/411; 548/450
[58] Field of Search .................. 548/450; 514/411

Primary Examiner—Donald G. Daus
Assistant Examiner—Robert Benson
Attorney, Agent, or Firm—Wenderoth, Lind & Ponack

[57] ABSTRACT

Indeno[1,2-b]pyrrole derivatives of the formula:

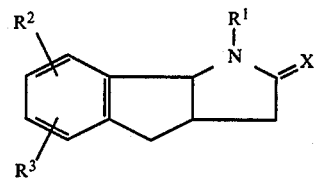

wherein $R^1$ is hydrogen, lower alkyl or carbamoylmethyl, $R^2$ is halogen or trifluoromethyl, $R^3$ is hydrogen or halogen, and X is oxygen or sulfur. These compounds are useful as medicines such as drugs for treating cerebral dysfunction, anticonvulsants, antiepileptics and antianxiety drugs.

10 Claims, No Drawings

INDENO(1,2-B)PYRROLE DERIVATIVES

TECHNICAL FIELD AND DISCLOSURE OF THE INVENTION

This invention relates to novel and therapeutically valuable hexahydro-indeno[1,2-b]pyrrole derivatives which are represented by the formula:

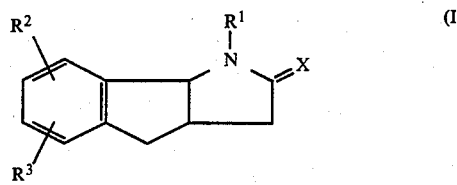
(I)

wherein $R^1$ is hydrogen, lower alkyl (methyl, ethyl, propyl, isopropyl, butyl, isobutyl, etc.) or carbamoylmethyl, $R^2$ is halogen (fluorine, chlorine, bromine or iodine) or trifluoromethyl, $R^3$ is hydrogen or halogen (the same as mentioned above), and X is oxygen or sulfur.

The compound of formula:

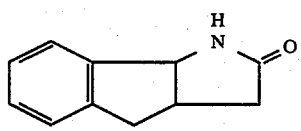

which is useful as an intermediate for the synthesis of compounds having blood sugar lowering action is described in J. Pharm. Sci., 62, 1363 (1973).

The present inventors have synthesized various compounds having a structure containing a 5-membered ring lactam which is formed by intramolecular cyclization of gamma-aminobutyric acid (hereinafter "GABA"), and investigated their utility. As a result, it has been found that compounds of the invention have the potent antagonistic activities against toxicity and convulsion induced by GABA antagonists such as picrotoxin or bicuculline, therefore they have GABA-like activities. Since GABA in itself, when administered peripherally, is said to be hard to transmit through the blood-brain barrier, GABA is not expected to exhibit its effects on the central nervous system. However, the compounds of the invention even when administered orally show the effects mentioned above, and so they are highly useful as medicines.

Moreover, the compounds of formula (I) have also antielectroshock and antimetrazole actions or electrocorticogram-improving action in a temporary cerebral ischemia model, antihypoxia effect and the like, and they are useful as medicines for treating cerebral dysfunction, anticonvulsants, antiepileptics and antianxiety drugs.

On the other hand, the known compounds mentioned above are extremely weak in such actions in comparison to the compounds of the invention or do not practically exhibit said activities.

The compounds of formula (I) can be produced in accordance with the conventional methods, for example, by the following reaction scheme:

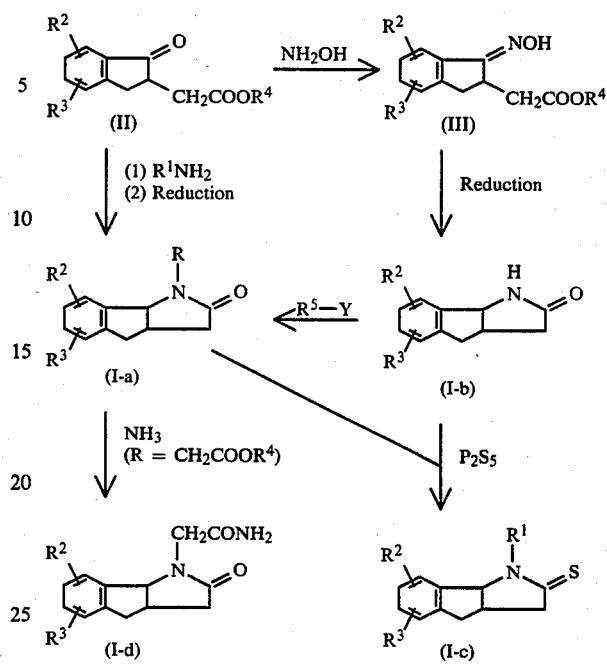

In the above reaction scheme, $R^1$, $R^2$ and $R^3$ are as defined above, R is $-CH_2COOR^4$ in addition to $R^1$, $R^4$ is lower alkyl, $R^5$ is lower alkyl or carbamoylmethyl, Y is a leaving reactive group such as halogen, $-SO_3H$, methylsulfonyloxy or p-tolylsulfonyloxy.

The objective compounds of the invention are the compounds of formula (I-a) wherein R is $R^1$, and compounds of formulas (I-b), (I-c) and (I-d).

In accordance with the reaction scheme, the methods for the production of the compounds of the invention will be explained more concretely.

The oxime derivative (III) which is obtained by the reaction of the compound (II) with hydroxylamine is subjected to catalytic reduction in the presence of a catalyst such as Raney nickel, platinum oxide or palladium carbon, preferably at 40-60 atm of hydrogen under heating to give the compound (I-b).

The compound (I-b) is allowed to react with an alkylating agent of the formula: $R^5-Y$ is an aprotic solvent such as dimethylformamide, dimethylsulfoxide, tetrahydrofuran or dioxane, or in a hydrocarbon solvent such as benzene or toluene, in the presence of sodium hydride or sodium alkoxide, at a temperature of from 0° C. to the boiling point of the solvent employed for several hours to give the compound (I-a). The compound (I-a) is also obtained by reacting the compound (II) in the presence of an amine of the formula: $R^1NH_2$ under the same reduction conditions mentioned above.

The compound (I-a) or (I-b) is allowed to react with diphosphorus pentasulfide in pyridine at 70°-100° C. for 4-5 hours to give the compound (I-c).

The compound of formula (I-a) wherein R is $-CH_2COOR^4$ is allowed to react with ammonia in a lower alkanol to give the compound (I-d).

The pharmacological properties of the compounds of the invention are shown below.

METHODS

1. Anti-picrotoxin Effect

Groups of 7-14 male dd-mice were used. Picrotoxin (5 mg/kg) was administered subcutaneously 60 minutes after the oral administration of test compound, and the 50% anti-lethal dose (ED$_{50}$) was calculated from the servival rate within 30 minutes.

2. Anti-bicuculline Effect

Groups of 4-14 male dd-mice were used. Bicuculline (0.6 mg/kg) was administered intravenously 60 minutes after the oral administration of test compound, and the ED$_{50}$, the dose required to protect 50% of the animals against tonic convulsion within 5 minutes was determined.

RESULTS

| Test Compound | Anti-picrotoxin-lethal effect, ED$_{50}$ mg/kg, p.o. | Anti-bicuculline-convulsive effect, ED$_{50}$ mg/kg, p.o. |
|---|---|---|
| A | 18 | 75 |
| B | 36 | 68 |
| C | 45 | 70 |
| D | 48 | 56 |
| E (Comparison) | >100 | >100 |

A: the compound of Example 1
B: the compound of Example 2
C: the compound of Example 8
D: the compound of Example 9
E: 1,2,3,3a,4,8b-Hexahydro-indeno[1,2-b]pyrrol-2-one (known compound)

The compounds of formula (I) of the invention can be administered orally or parenterally in the form of pharmaceutical compositions with a suitable and conventional, pharmaceutically acceptable carriers.

The pharmaceutical compositions can take tablets, capsules, granules, powder, injectable solutions or the like.

The daily dose for human adults usually ranges from about 10 mg to about 500 mg for oral administration, in single or multiple doses, but the dose may vary depending upon the age, the body weight and/or the conditions of a patient to be treated and the response to the medication.

The present invention will be explained more concretely by the following examples, but they are not to be construed as limiting the present invention.

EXAMPLE 1

Methyl 4-chloro-1-hydroxyimino-2,3-dihydro-inden-2-acetate (15 g) is hydrogenated at 40 atm of hydrogen in 200 ml of methanol plus 50 ml of acetic acid in the presence of 1.5 g of platinum oxide catalyst at 30°-50° C. for 7 hours. The catalyst is then filtered off, and the filtrate is concentrated. The residual oil is extracted with chloroform. The extract is washed with aqueous potassium carbonate solution, then with water and dried over sodium sulfate, and the solvent is distilled off. The residue is heated on an oil bath at 110°-120° C. for 2 hours. After cooling, ether is added, and the precipitated crystals are collected by filtration and recrystallized from ether to give 5 g of 5-chloro-1,2,3,3a,4,8b-hexahydro-indeno[1,2-b]pyrrol-2-one, melting at 186°-187° C.

EXAMPLE 2

A solution of 2 g of 5-chloro-1,2,3,3a,4,8b-hexahydro-indeno[1,2-a]pyrrol-2-one in 15 ml of dimethylformamide is added dropwise under ice-cooling to a suspension of 1 g of sodium hydride (60% dispersion in mineral oil) in 20 ml of dimethylformamide. After stirring at 40°-50° C. for 1 hour, 3 g of methyl iodide is added dropwise to the ice-cooled mixture, and the whole is stirred at 30°-40° C. for 2 hours. The reaction mixture is then poured into ice-cold water, neutralized with dilute hydrochloric acid and extracted with ethyl acetate. The extract is washed with water and dried over sodium sulfate, and the solvent is distilled off. The residual oil is chromatographed over silica gel with chloroform eluant. The purified product is crystallized with a mixture of isopropyl ether and hexane, and recrystallized from the same mixture to give 1.6 g of 5-chloro-1-methyl-1,2,3,3a,4,8b-hexahydro-indeno[1,2-a]pyrrol-2-one, melting at 107°-109° C.

EXAMPLE 3

To a solution of 4.2 g of 7-chloro-1,2,3,3a,4,8b-hexahydro-indeno[1,2-b]pyrrol-2-one in 100 ml of pyridine is added 2.2 g of diphosphorus pentasulfide, and the mixture is stirred at 90° C. for 1 hour. The reaction mixture is then cooled, poured into ice-cold water and extracted with ethyl acetate. The extract is washed with water and dried over sodium sulfate, and the solvent is distilled off. The residual oil is chromatographed over silica gel with chloroform eluant. The purified product is crystallized with isopropyl ether and recrystallized from the same solvent to give 2.5 g of 7-chloro-1,2,3,3a,4,8b-hexahydro-indeno[1,2-b]pyrrol-2-thione, melting at 225°-227° C.

EXAMPLE 4

To a solution of 2.7 g of 5-chloro-1,2,3,3a,4,8b-hexahydro-indeno[1,2-b]pyrrol-2-one in 80 ml of dimethylformamide is added 0.8 g of sodium hydride (60% dispersion in mineral oil). After the evolution of gas ceases, the mixture is heated at 50°-60° C. for 1 hour whereupon a solution of 1.8 g of monochloroacetamide in 30 ml of dimethylformamide is added dropwise, and the resulting mixture is stirred at the same temperature for 2 hours and then cooled. The reaction mixture is poured into ice-cold water, acidified with dilute hydrochloric acid and extracted with chloroform. The extract is dried over sodium sulfate, and the solvent is distilled off. The residue is crystallized with a mixture of acetone and ether. The crystalline product is collected by suction filtration and recrystallized from ether to give 1.4 g of [5-chloro-1,2,3,3a,4,8b-hexahydro-2-oxo-indeno[1,2-b]pyrrol-1-yl]acetamide, melting at 186°-188° C.

The following compounds can be produced in the same manner of the above Examples 1-4.

(5) 6-Chloro-1,2,3,3a,4,8b-hexahydro-indeno[1,2-b]pyrrol-2-one, melting at 164°-166° C.

(6) 7-Chloro-1,2,3,3a,4,8b-hexahydro-indeno[1,2-b]pyrrol-2-one, melting at 220°-223° C.

(7) 6-Fluoro-1,2,3,3a,4,8b-hexahydro-indeno[1,2-b]pyrrol-2-one, melting at 166°-168° C.

(8) 6-Fluoro-1,2,3,3a,4,8b-hexahydro-indeno[1,2-b]pyrrol-2-thione, melting at 188°-191° C.

(9) 7-Fluoro-1,2,3,3a,4,8b-hexahydro-indeno[1,2-b]pyrrol-2-one, melting at 186°-188° C.

(10) 5-Fluoro-1,2,3,3a,4,8b-hexahydro-indeno[1,2-b]pyrrol-2-one, melting at 183°-185° C.

(11) [5-Fluoro-1,2,3,3a,4,8b-hexahydro-indeno[1,2-b]pyrrol-1-yl]acetamide, melting at 172°-174° C.

(12) 6-Fluoro-1-methyl-1,2,3,3a,4,8b-hexahydro-indeno[1,2-b]pyrrol-2-one, melting at 78°–81° C.

(13) 5,7-Dichloro-1,2,3,3a,4,8b-hexahydro-indeno[1,2-b]pyrrol-2-one, melting at 181°–184° C.

(14) 5-Bromo-1,2,3,3a,4,8b-hexahydro-indeno[1,2-b]pyrrol-2-one, melting at 192°–201° C.

(15) 7-Trifluoromethyl-1,2,3,3a,4,8b-hexahydro-indeno[1,2-b]pyrrol-2-one

Although the present invention is described in detail hereinbefore, namely in the specification and the examples contained therein, other embodiments and modification of the invention are possible without departing from the spirit and scope of the invention.

What is claimed is:

1. An indeno[1,2-b]pyrrole compound of the formula:

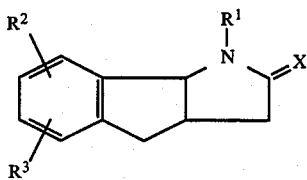

wherein $R^1$ is hydrogen, lower alkyl or carbamoylmethyl, $R^2$ is halogen or trifluoromethyl, $R^3$ is hydrogen or halogen, and X is oxygen or sulfur.

2. The compound as defined in claim 1 which is 5-chloro-1,2,3,3a,4,8b-hexahydro-indeno[1,2-b]pyrrol-2-one.

3. The compound as defined in claim 1 which is 5-chloro-1-methyl-1,2,3,3a,4,8b-hexahydro-indeno[1,2-b]pyrrol-2-one.

4. The compound as defined in claim 1 which is 6-chloro-1,2,3,3a,4,8b-hexahydro-indeno[1,2-b]pyrrol-2-one.

5. The compound as defined in claim 1 which is 7-chloro-1,2,3,3a,4,8b-hexahydro-indeno[1,2-b]pyrrol-2-one.

6. The compound as defined in claim 1 which is 6-fluoro-1,2,3,3a,4,8b-hexahydro-indeno[1,2-b]pyrrol-2-one.

7. The compound as defined in claim 1 which is 6-fluoro-1,2,3,3a,4,8b-hexahydro-indeno[1,2-b]pyrrol-2-thione.

8. The compound as defined in claim 1 which is 7-fluoro-1,2,3,3a,4,8b-hexahydro-indeno[1,2-b]pyrrol-2-one.

9. The compound as defined in claim 1 which is 5-fluoro-1,2,3,3a,4,8b-hexahydro-indeno[1,2-b]pyrrol-2-one.

10. A pharmaceutical composition useful for treatment of convulsion, epilepsy and anxiety comprising a pharmaceutically acceptable carrier and a therapeutically effective amount for said treatment, of a compound as defined in claim 1.

* * * * *